US00PP20589P3

(12) United States Plant Patent
Blom

(10) Patent No.: US PP20,589 P3
(45) Date of Patent: Dec. 22, 2009

(54) ***CHRYSANTHEMUM* PLANT NAMED 'ZANMUFLAMIN'**

(50) Latin Name: *Chrysanthemum×morifolium*
Varietal Denomination: Zanmuflamin

(75) Inventor: Wilhelmus Bernardus Blom, Leimuiden (NL)

(73) Assignee: Chrysanthemum Breeders Association Research B.V., Valkenburg (NL)

( * ) Notice: Subject to any disclaimer, the term of this patent is extended or adjusted under 35 U.S.C. 154(b) by 25 days.

(21) Appl. No.: 12/003,596

(22) Filed: Dec. 28, 2007

(65) Prior Publication Data

US 2009/0172854 P1 Jul. 2, 2009

(51) Int. Cl.
*A01H 5/00* (2006.01)

(52) U.S. Cl. ..... Plt./292

(58) Field of Classification Search ..... Plt./292
See application file for complete search history.

*Primary Examiner*—Susan B McCormick Ewoldt
(74) *Attorney, Agent, or Firm*—Steptoe & Johnson LLP

(57) ABSTRACT

A *Chrysanthemum* plant named 'Zanmuflamin' characterized by its medium sized double type blooms with bright purple ray florets and prolific branching; natural season flower date September 11 (week 37); blooming for a period of 5 weeks.

3 Drawing Sheets

Botanical designation: *Chrysanthemum×morifolium* Ramat.

Cultivar denomination: 'Zanmuflamin'.

BACKGROUND OF THE INVENTION

'Zanmuflamin' is a product of a breeding and selection program for outdoor pot mums (garden mums) which had the objective of creating new *Chrysanthemum* cultivars with a double type flower, a natural season flower date around September 10 (week 37); blooming for a period of 5 weeks. The new plant of the present invention comprises a new and distinct cultivar of *Chrysanthemum* plant 'Zanmuflamin' is a seedling resulting from a crossing of the female plant id 16,609 and the male plant id 871. Plants of the new cultivar 'Zanmuflamin' differ from the parent plants in the following characteristics (1) bloom type and (2) color ray-florets. (1) The bloom type of 'Zanmuflamin' is double, while that of the female parent is double—spider, and of the male parent double—pompon. (2) The ray-florets of 'Zanmuflamin' are bright pink, while those of the female parent are salmon, and of the male parent red.

The new and distinct cultivar was discovered and selected as a flowering plant by Wilhelmus Bernardus Blom on a cultivated field in Rijsenhout, The Netherlands in 2004. The first act of asexual reproduction of 'Zanmuflamin' was accomplished when vegetative cuttings were taken from the initial selection in 2004 and propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct variety of *chrysanthemum* (of ca. 17 weeks) is shown in the accompanying drawings, the color being as nearly true as possible with color photographs of this type.

DESCRIPTION OF THE INVENTION

Figure 1:
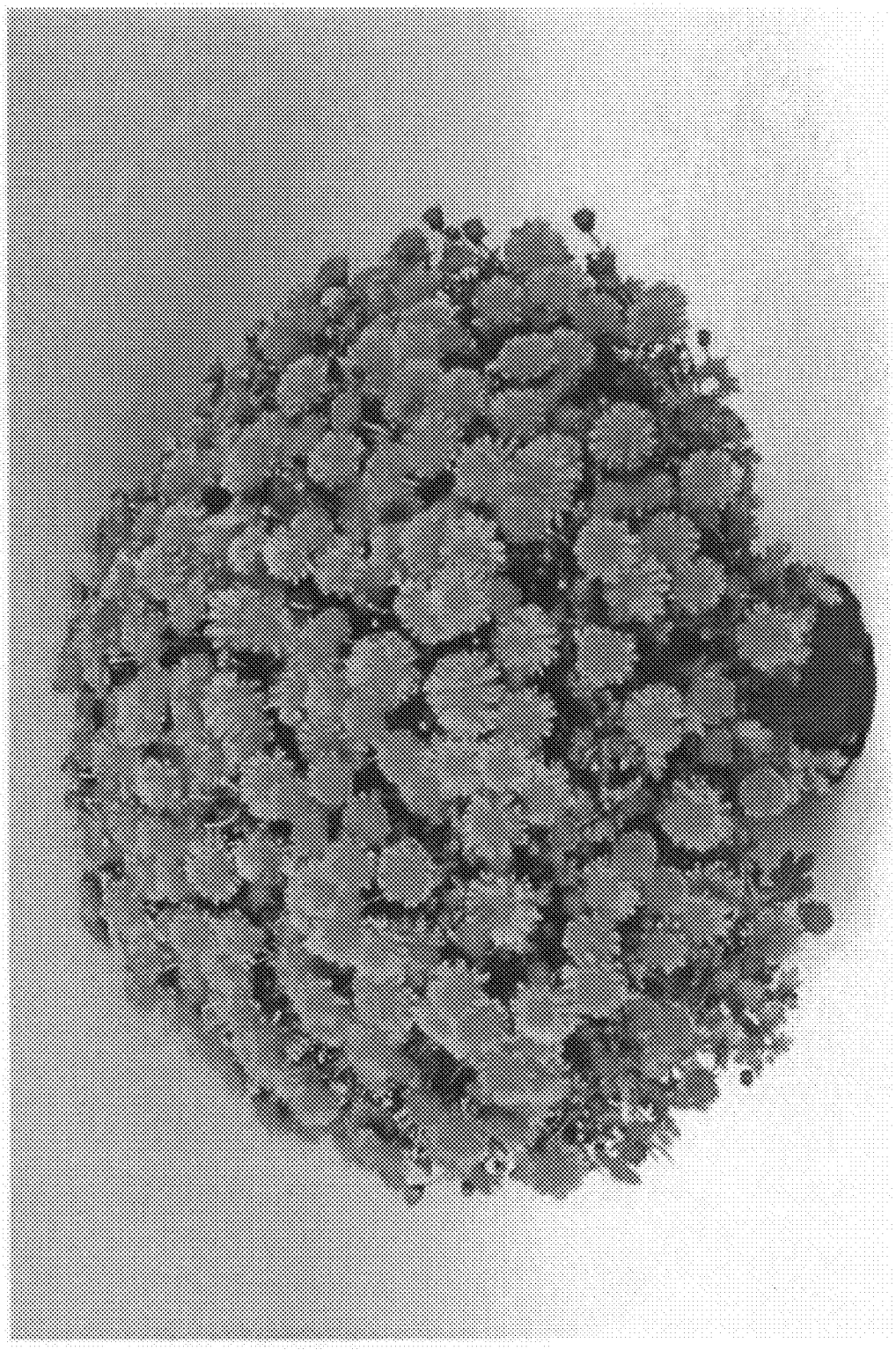
FIG. 1 shows a plant of the cultivar in full bloom.
Figure 2:
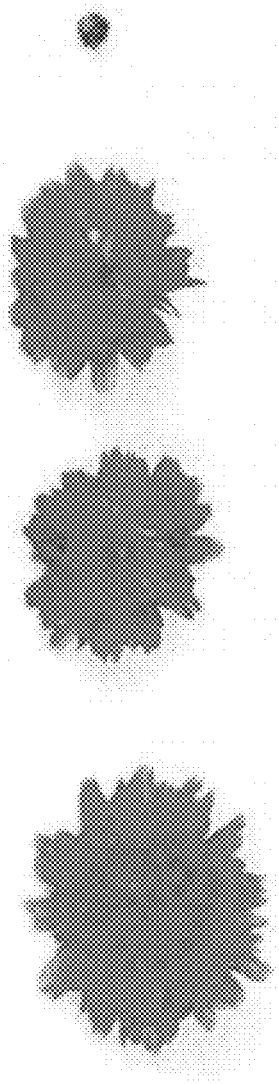
FIG. 2 shows the various stages of bloom of the new cultivar.
Figure 3:
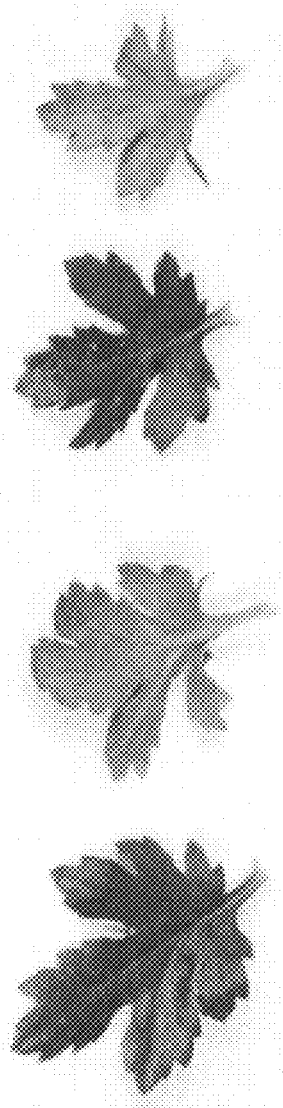
FIG. 3 shows the various stages of foliage of the new cultivar.

The observations and measurements were gathered from plants grown out door in Rijsenhout, The Netherlands under natural day length and temperature and planted in week 23 in 2006. The natural blooming date of this crop was September 11 (week 37). The average height of the plants was 30 cm. No growth retardants were used. No tests were done on disease or insect resistance or susceptibility. No tests were done on cold or drought tolerance. This new variety produces medium sized double type blooms with bright purple ray florets blooming for a period of 5 weeks.

From the cultivars known to inventor the most similar existing cultivar in comparison to 'Zanmuflamin' is 'Venus' (U.S. Plant Pat. No. 14,378). When 'Venus' and 'Zanmuflamin' are being compared the following difference is noticed: The difference of 'Venus' and 'Zanmuflamin' are (1) flower colour and (2) natural season blooming date. (1) The flower colour of 'Zamuflamin' is more pink than of 'Venus' (2) 'Venus' flowers later than 'Zanmuflamin'.

The following is a description of the plant and characteristics that distinguish 'Zanmuflamin' as a new and distinct variety. The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

Botanical Description of *Chrysanthemum xmorifolium* Ramat. 'Zanmuflamin'

| | |
|---|---|
| Bud | |
| Size | Small; cross-section 1 cm, height 0.8 cm |
| Outside Color | Greyed-purple 186D |

TABLE 1-continued

| Botanical Description of *Chrysanthemum xmorifolium* Ramat. 'Zanmuflamin' | |
|---|---|
| Phyllaries | 2 rows |
| Phyllaries among disc-florets | Not present |
| Bloom | |
| Type | Double |
| Height | 1.5 cm |
| Size | 4.5 cm |
| Phyllary number | 12-14 |
| Phyllary color | Green 138A |
| Phyllary length and width | 2 cm and 2 mm |
| Peduncle length | 4-4.5 cm |
| Peduncle color | Green 138B |
| Number of blooms per branch | Approx. 5 blooms per branch |
| Performance on the plant | 5 weeks |
| Seeds | Produced in small quantities, ovate grey-brown 199A, 1½ mm in length. |
| Fragrance | Typical *chrysanthemum,* slightly |
| Color | |
| Center of the flower | Immature stage: Red-purple 58A Mature stage (17 weeks): Red-purple 58A |
| Color of upper surface of the ray-florets | Red-purple 59D |
| Color of the lower surface of the ray-florets | Greyed-purple 186C (at top) to 186D (at base) |
| Tonality from Distance | A garden mum with bright purple flowers |
| Color of the ray-florets after aging of the plant | Greyed-purple 186B |
| Ray florets | |
| Texture | Upper and under side smooth |
| Number | 200-220 |
| Cross-section | Flat |
| Longitudinal axis of majority | Straight |
| Length of corolla tube | 0.3-0.4 cm |
| Ray-floret margin | Entire |
| Ray-floret length | 2-2.2 cm |
| Ray-floret width | 0.3-0.5 cm |
| Ratio length/width | High |
| Shape of tip | Rounded |
| Disc florets | Absent |
| Receptacle shape | Conical raised |
| Reproductive Organs | |
| Stamen | Lacking |
| Styles | Short |
| Style color | Yellow 13A |
| Style Length | 3 mm |
| Stigma color | Yellow-green 144A |
| Stigma Width | 1 mm |
| Ovaries | Enclosed in calyx |
| Plant | |
| Form | Grown as a spray type pot mum, outdoor mounded and round |

TABLE 1-continued

| Botanical Description of *Chrysanthemum xmorifolium* Ramat. 'Zanmuflamin' | |
|---|---|
| Growth habit | Spherical shape |
| Growth rate | Medium vigour |
| Height | 30 cm |
| Width | 40 cm |
| Stem Color | Greyed-brown 199C |
| Stem Strength | Strong |
| Stem Brittleness | Not brittle |
| Stem Anthocyanin Coloration | Present, Greyed-Purple 185C |
| Internode length | 1-2 cm |
| Length of lateral branch | From top to bottom 15-18 cm |
| Lateral branch color | Yellow-green 146C |
| Lateral branch, attachment | Medium strength |
| Branching (average number of lateral branches) | Good with 6-7 breaks after pinching |
| Natural season blooming date | September 11 (week 37) |
| Foliage | |
| Leaf color | Upper side Green 143b Lower side Green 143C |
| Color midvein | Upper side Yellow-green 147D Lower side Yellow-green 148D |
| Size | Small.; length 4.5-6.5 cm. width 3-3.5 cm |
| Quantity (number per lateral branch) | 16 |
| Shape | Elliptic |
| Texture upper side | Glabrous |
| Texture under side | Pubescent |
| Venation arrangement | Palmate |
| Shape of the margin | Serrated |
| Shape of Base of Sinus Between Lateral Lobes | Acute |
| Margin of Sinus Between Lateral Lobes | Diverging |
| Shape of Base | Truncate |
| Apex | Mucronulate |
| Petiole length | 1 cm |
| Petiole color | Yellow-green 147D |

TABLE 2

| Differences with the comparison variety (grown under identical conditions) | | |
|---|---|---|
| | 'Zanmuflamin' | 'Venus' |
| Flower colour | Red-purple 59D | Red-purple 60A |
| Natural season blooming date | September 11 (week 37) | September 18 (week 38) |

I claim:

1. A new and distinct variety of *Chrysanthemum* plant as described and illustrated.

* * * * *